United States Patent [19]

Kubota

[11] Patent Number: 4,917,828

[45] Date of Patent: Apr. 17, 1990

[54] PROCESS FOR PREPARING KETOCHOLANATES

[75] Inventor: Naohiro Kubota, Urawa, Japan

[73] Assignee: Adeka Argus Chemical Co., Ltd., Tokyo, Japan

[21] Appl. No.: 170,684

[22] Filed: Mar. 14, 1988

[30] Foreign Application Priority Data

Mar. 31, 1987 [JP] Japan .................. 62-78105

[51] Int. Cl.$^4$ .............. C07J 1/100; A61K 31/56
[52] U.S. Cl. ................. 260/397.3; 260/397.4; 260/397.5; 260/687 R; 514/169
[58] Field of Search ............ 514/169, 397.4; 260/397.1, 397.2, 397.3, 687 R, 397.5

[56] References Cited
PUBLICATIONS

Chem. Abstracts 90(9): 72386 (2/26/79).
Chem. Abstracts 89(13): 110128 (9/25/78).
Chem. Abstracts 92(7): 59113 and 59114 (2/18/80).

*Primary Examiner*—Shep K. Rose
*Assistant Examiner*—Raymond J. Henley, III
*Attorney, Agent, or Firm*—Young & Thompson

[57] ABSTRACT

A process for preparing ketocholanate(s) comprises oxidizing cholanic acid compound(s), such as alkyl 3α-alkoxycarbonyloxy-7α,12α- dihydroxycholanates or alkyl 3α-acyloxy-7α,12α-dihydroxycholanates, with an alkali metal salt of an oxo acid of halogen in the presence of a cerium compound. Ketocholanate(s) such as alkyl 3α-alkoxycarbonyloxy-7,12-dioxocholanataes, alkyl 3α-alkoxycarbonyloxy- 7-oxo-12α-hydroxycholanates, alkyl 3α-acyloxy-7,12-dioxocholanates, alkyl 3α-alkoxycarbonyloxy-12- oxocholantes, alkyl 3α-acyloxy-7-oxo-12α-hydroxycholanates and mixtures thereof are thus produced.

8 Claims, No Drawings

PROCESS FOR PREPARING KETOCHOLANATES

BACKGROUND OF THE INVENTION

1. Field of the Invention:

This invention relates to a process for preparing a ketocholanate comprising oxidizing a cholanate which has a protected hydroxyl group at the 3-position and hydroxyl group(s) at the 12-position and optionally at the 7-position with an alkali metal salt of an oxo acid of halogen in the presence of a cerium compound.

2. Description of the Prior Art:

Ketocholanic acid and its derivatives are known to be effective in accelerating the absorption of fat-soluble vitamins and the secretion of bile as well as in treating various hepatic disorders. Further these compounds are important as intermediates in the synthesis of dehydrocholic acid or chenodeoxycholic acid.

There have been reported a number of processes for the oxidation of cholanic acid derivatives having hydroxyl group(s).

For example, French Pat. No. 854817 has disclosed a process for preparing 7-keto-3$\alpha$, 12$\alpha$,-dihydroxycholanic acid by adding an equimolar amount of bromine to an aqueous solution of cholic acid and sodium bicarbonate to thereby selectively oxidize the cholic acid. U.S. Pat. No. 2576728 has disclosed a process for preparing 3,7,12-triketocholanic acid by selectively and completely oxidizing 7-keto-3$\alpha$, 12$\alpha$-dihydroxycholanic acid in an aqueous solution of a mixture of sodium hydroxide, sodium bicarbonate and sodium bromide at a low temperature with the use of chlorine gas. Japanese Patent Publication No. 20493/ 1970 has disclosed a process for preparing keto bile acids by oxidizing bile acids having hydroxyl group(s) with antiformin in the presence of an alkali metal acetate. However each of these known processes has some disadvantages such as a poor yield and/or a low purity of the desired product or a prolonged reaction time and thus is unsatisfactory from the practical viewpoint.

Therefore there has been generally employed a process for oxidizing cholanic acid which comprises first esterifying a carboxylic acid with an alcohol, protecting, if necessary, the hydroxyl group(s) not to be converted into keto group(s) by, for example, acylation, and then oxidizing the product.

It is known that a heavy metal oxidizing agent such as chromic acid, potassium chromate or sodium bichromate is employed in the above oxidation. Thus this process is accompanied by some disadvantages such that the waste water thereof contains toxic chromium compound(s) and that the product per se may be contaminated with the same. Accordingly there have been proposed processes wherein no heavy metal oxidizing agent is used. Examples of these processes include one wherein cholic acid is oxidized in a solvent mixture comprising a fatty acid and an alcohol with an aqueous alkaline solution of sodium hypochlorite (cf. Japanese Patent Laid-Open No. 51259/1974); and another one wherein the oxidation is carried out in a nonaqueous solvent with the use of bromocarbamide (cf. Japanese Patent Publication No. 41420/1981).

However each of these processes has some disadvantages such as a poor yield and/or a low purity of the desired product or a prolonged reaction time. Thus it has been required to improve the same.

SUMMARY OF THE INVENTION

It is an object of the present invention to provide a process for readily and efficiently preparing a ketocholanate having protected hydroxyl group(s) which comprises oxidizing a cholate or deoxycholate protected at the 3-position.

We have attempted to achieve the above object and consequently found that the desired ketocholanate can be efficiently prepared within a remarkably short period of time by oxidizing a cholate or deoxycholate protected at the 3-position with the use of an alkali metal salt of an oxo acid of halogen in the presence of a cerium compound, thus completing the present invention.

Accordingly the present invention provides a process for preparing ketocholanate(s) which comprises oxidizing one or more starting compounds selected from among alkyl 3$\alpha$-alkoxycarbonyloxy-7$\alpha$,12$\alpha$-dihydroxycholanates, alkyl 3$\alpha$-acyloxy-7$\alpha$,12$\alpha$-dihydroxycholanates, alkyl 3$\alpha$-alkoxy-carbonyloxy12$\alpha$-hydroxycholanates and alkyl 3$\alpha$-acyloxy-12$\alpha$-hydroxycholanates with an alkali metal salt of an oxo acid of halogen in the presence of a cerium compound to thereby give one or more compounds selected from among alkyl 3$\alpha$-alkoxycarbonyloxy-7,12-dioxocholanates, alkyl 3$\alpha$-alkoxycarbonyl-oxy-7-oxo-12$\alpha$-hydroxycholanates, alkyl 3$\alpha$-acyloxy-7,12-dioxocholanates, alkyl 3$\alpha$-acyloxy-7-oxy-12$\alpha$-hydroxy-cholanates, alkyl 3$\alpha$-alkoxycarbonyloxy-12-oxocholanates, alkyl 3$\alpha$-acyloxy-12-oxocholanates and mixtures thereof.

DETAILED DESCRIPTION OF THE INVENTION

The cholanate to be used as the starting compound in the process of the present invention has a hydroxyl group protected with an alkoxycarbonyloxy or acyloxy group at the 3-position and hydroxyl group(s) at the 12-position and optionally at the 7-position. Examples of the alkoxy group in said protective alkoxycarbonyloxy group include methoxy, ethoxy, propoxy, isopropoxy, butoxy, octoxy and 2-ethylhexyloxy groups. Examples of the acyl group in said acyloxy group include acetyl, propionyl, butyryl, octanoyl, benzoyl and succinoyl groups. Examples of the alkyl group forming the alkyl esters include methyl, ethyl, propyl, isopropyl, butyl, isobutyl, sec-butyl, tert-butyl, amyl, hexyl, octyl and 2-ethylhexyl groups.

Compounds having these protective groups are known and can be readily obtained by, for example, reacting a cholanate having hydroxyl group(s) with an alkyl chloroformate or an acid anhydride.

As the cerium compound to be used as a catalyst in the process of the present invention, either a cerium compound of a high purity or a mixture of rare earth compounds containing a large amount of cerium may be employed. Examples thereof include cerium chloride (rare earth chlorides), cerium fluoride (rare earth fluorides), cerium oxide (rare earth oxides), cerium hydroxide (rare earth hydroxides), cerium carbonate (rare earth carbonates) cerium sulfate (rare earth sulfates), cerium oxalate (rare earth oxalates), cerium acetate (rare earth acetates), cerium nitrate (rare earth nitrates), ammonium ceric nitrate and ammonium ceric sulfate. Among these compounds, ceric compounds such as ammonium ceric nitrate and ammonium ceric sulfate.

The amount of the cerium compound is not particularly restricted. It is generally approximately 0.1 to 100

% by mol, preferably 0.5 to 10 % by mol, based on the cholanic acid compound(s).

Examples of the alkali metal salt of an oxo acid of halogen to be used in the process of the present invention as an oxidizing agent include sodium, potassium and lithium salts of an oxo acid of halogen, such as chloric, bromic, iodic, chlorous, bromous, hypochlorous and perchloric acids.

The oxidizing agent should be employed in an equimolar amount or above to the hydroxyl group(s) to be oxidized. When the oxidation is to be completely effected, the amount of the oxidizing agent is not restricted so long as it is more than the equivalent level. Since the reaction rate increases with an increase in the amount of the oxidizing agent, it is generally employed in an amount up to approximately five equivalents. When the oxidation is to be partially effected, it is preferable that the oxidizing agent is employed in an amount of one to approximately two equivalents to the hydroxyl group(s) to be oxidized. This is because the use of a large excess of the oxidizing agent might not accelerate the aimed oxidation but cause the oxidation of hydroxyl group(s) which are not to be oxidized.

In the process of the present invention, the oxidation is carried out in a solvent. Examples of the solvent include water; lower alcohols such as methanol, ethanol and isopropanol; organic nitriles such as acetonitrile and propionitrile; halogenated hydrocarbons such as dichloroethane, chloroform and carbon tetrachloride; lower aliphatic acids such as acetic acid and propionic acid; ethers such as dioxane and tetrahydrofuran; and aliphatic ketones such as acetone and methyl ethyl ketone.

These solvents may be employed in an amount of one to 50 times by weight as much as the cholanic acid compound(s).

The reaction temperature may be from room temperature to the reflux temperature of the solvent. It is preferable to carry out the reaction at a temperature of 30° C or above to shorten the reaction time.

To further illustrate the present invention, the following Examples will be given.

EXAMPLE 1

Preparation of methyl 3α-ethoxycarbonyloxy-7-oxo-12α-hydroxycholanate 25 g of methyl 3α-ethoxycarbonyloxy-7α,12α-dihydroxycholanate was added to a mixture comprising 360 m of acetonitrile, 120 m of water and 120 m of dichloroethane. While stirring the mixture at room temperature, 5.0 g of sodium bromate and 1.8 g of ammonium ceric sulfate were successively added thereto.

The resulting mixture was stirred at 40 to 45° C. for three hours and then cooled. Then 150 m of toluene was added thereto. The aqueous phase was discarded and the organic phase was washed with a 5 % solution of sodium thiosulfate and then with water thoroughly.

The resulting organic phase was dried and the solvent was removed therefrom to thereby give a pale yellow solid. The analysis of the product with liquid chromatography revealed that the conversion was 98 %.

This product was recrystallized from methanol to thereby give the aimed product in the form of a white solid (m.p.: 185 to 188° C.). The IR and NMR spectra of this product completely agreed with those of a standard specimen.

EXAMPLE 2

Preparation of methyl 3α-ethoxycarbonyloxy-7,12-dioxocholanate 25 g of methyl 3α-ethoxycarbonyloxy-7α,12α-dihydroxy-cholanate was added to a mixture comprising 360 m of acetonitrile, 120 m of water and 120 m of dichloroethane. While stirring the mixture at room temperature, 15 g of sodium bromate and 5.5 g of ammonium ceric nitrate were successively added thereto.

The resulting mixture was stirred under reflux for three hours and then 150 m of toluene was added thereto. The aqueous phase was discarded and the organic phase was washed with a 5 % solution of sodium thiosulfate and then with water thoroughly.

The resulting organic phase was dried and the solvent was removed therefrom to thereby give a pale yellow solid. The analysis of the product with liquid chromatography revealed that the reaction proceeded quantitatively.

This product was recrystallized from methanol to thereby give the aimed product in the form of a white solid (m.p.: 127 to 129° C.). The IR and NMR spectra of this product completely agreed with those of a standard specimen.

EXAMPLE 3

Preparation of methyl 3α-acetoxy-7,12-dioxocholanate 22.5 g of methyl 3α-acetoxy-7α,12α-dihydroxycholanate was added to a mixture comprising 360 m of acetonitrile, 120 m of water and 120 m of dichloroethane. While stirring the mixture at room temperature 15 g of sodium bromate and 5.5 g of ammonium ceric nitrate were successively added thereto.

The resulting mixture was stirred under reflux for three hours and then 150 m of toluene was added thereto. The aqueous phase was discarded and the organic phase was washed with a 5 % solution of sodium thiosulfate and then with water thoroughly.

The resulting organic phase was dried and the solvent was removed therefrom to thereby give a pale yellow solid. The analysis of this product with liquid chromatography revealed that the reaction proceeded quantitatively.

This product was recrystallized from methanol to thereby give the aimed compound in the form of a white solid (m.p.: 152 to 155° C.). The IR and NMR spectra of this product completely agreed with those of a standard specimen.

COMPARATIVE EXAMPLE

Oxidation of methyl 3α-ethoxycarbonyloxy-7α,12α-dihydroxycholanate 25 g of 3α-ethoxycarbonyloxy-7α,12α-dihydroxycholanate was added to a mixture comprising 360 mαof acetonitrile, 120 mαof water and 120 mαof dichloroethane. While stirring the mixture at room temperature, 5 g of sodium bromate was added thereto.

The resulting mixture was stirred at 40° C. to 45° C. for three hours. The analysis of this mixture with liquid chromatography revealed that the reaction did not proceed at all. Thus 10 g of sodium bromate was further added thereto and the mixture was stirred under reflux for additional three hours but the reaction did not yet proceed at all.

What is claimed is:

1. A process for preparing ketocholanates, comprising oxidizing at least one starting compound selected from the group consisting of a $C_{1-8}$ alkyl 3α-alkoxycarbonyloxy7α,12α-dihydroxycholanate, a $C_{1-8}$ alkyl 3α-acyloxy-7α,12α-dihydroxycholanate, a $C_{1-8}$ alkyl 3α-alkoxycarbonyloxy-12α-hydroxycholanate and a $C_{1-8}$ alkyl 3α-acyloxy-12α-hydroxycholanate with an alkali metal salt of an oxo acid of halogen in the presence of a cerium compound, thereby to produce at least one compound selected from the group consisting of a $C_{1-8}$ alkyl 3α-alkoxycarbonyloxy-7,12-dioxochalanate, a $C_{1-8}$ alkyl 3α-alkoxy-carbonyloxy-7-oxo-12α-hydroxycholanate, a $C_{1-8}$ alkyl 3a-acyloxy-7,12-dioxocholanate, a $C_{1-8}$ alkyl 3a-acyloxy-7-oxo-12α-hydroxycholanate, a $C_{1-8}$ alkyl 3α-alkoxycarbonyloxy-12-oxocholanate, and a $C_{1-8}$ alkyl 3α-acyloxy-12-oxocholanate.

2. The process for preparing ketocholanates as set forth in claim 1, comprising oxidizing a $C_{1-8}$ alkyl 3α-alkoxycarbonyloxy-7α,12α-dihydroxycholanate or a $C_{1-8}$ alkyl 3α-acyloxy-7α-dihydroxycholanate with from about one to about two equivalents an alkali metal salt of an oxo acid of halogen in the presence of a cerium compound thereby to produce a $C_{1-8}$ alkyl 3α-alkoxycarbonyloxy-7-oxo-12α-hydroxycholanate or a $C_{1-8}$ alkyl 3α-acyloxy-7-oxo-12α-hydroxycholanate.

3. The process for preparing ketocholanates as set forth in claim 1, comprising oxidizing a $C_{1-8}$ alkyl 3α-acyloxy-7α,12α-dihydroxycholanate or a $C_{1-8}$ alkyl 3α-alkoxycarbonyloxy-7α,12α-dihydroxycholanate with from about two to about five equivalents of an alkali metal salt of an oxo acid of halogen in the presence of a cerium compound thereby to produce a $C_{1-8}$ alkyl 3α-acyloxy-7,12-dioxocholanate or a $C_{1-8}$ alkyl 3α-alkoxycarbonyloxy-7,12-dioxocholanate.

4. The process according to claim 1, wherein said oxidizing step is carried out in a solvent, at a temperature from about room temperature to about the reflux temperature of the solvent.

5. The process according to claim 4, wherein said solvent is used in an amount of about 1 to about 50 times by weight of said at least one starting compound.

6. The process according to claim 1, wherein said cerium compound is used in an amount of about 0.1 to about 100 mol %, based on said at least one starting compound.

7. The process according to claim 6, wherein said cerium compound is used in an amount of about 0.5 to about 10 mol %, based on said at least one starting compound.

8. The process according to claim 1, wherein said alkali metal salt of an oxo acid of halogen is used in an amount from about one to about five equivalents, relative to said at least one starting compound.

* * * * *